US007635769B2

(12) United States Patent
Uhlmann et al.

(10) Patent No.: US 7,635,769 B2
(45) Date of Patent: Dec. 22, 2009

(54) OLIGORIBONUCLEOTIDE DERIVATIVES FOR SPECIFIC INHIBITION OF GENE EXPRESSION

(75) Inventors: Eugen Uhlmann, Glashutten (DE); Jochen Huber, Maxdorf (DE); Niki Gunkel, Heidelberg (DE); Sandra Neumann, Offenbach (DE)

(73) Assignee: Sanofi-Aventis Drutschland, Frankfurt am Main (DE)

( * ) Notice: Subject to any disclaimer, the term of this patent is extended or adjusted under 35 U.S.C. 154(b) by 115 days.

(21) Appl. No.: 11/233,907

(22) Filed: Sep. 22, 2005

(65) Prior Publication Data

US 2006/0025374 A1   Feb. 2, 2006

Related U.S. Application Data

(63) Continuation of application No. 10/192,926, filed on Jul. 11, 2002, now abandoned.

(30) Foreign Application Priority Data

Jul. 12, 2001   (DE) ................. 101 33 915

(51) Int. Cl.
    C07H 21/00   (2006.01)
    C07H 21/02   (2006.01)
    C07H 21/04   (2006.01)
    C12Q 1/68    (2006.01)
    C12N 15/63   (2006.01)

(52) U.S. Cl. .................. 536/24.5; 435/6; 435/91.1; 435/455; 536/23.1; 536/24.3; 536/25.2; 536/25.3

(58) Field of Classification Search .............. 435/6, 435/91.1, 91.31, 455; 514/44; 536/23.1, 536/24.3, 24.5, 25.2, 25.3
See application file for complete search history.

(56) References Cited

U.S. PATENT DOCUMENTS 5,886,165 A   3/1999   Kandimalla et al.

FOREIGN PATENT DOCUMENTS

CA   2087818   7/1993
EP   0552766   1/1993

OTHER PUBLICATIONS

Peracchi, A. et al., Rev. Med. Virol., vol. 14, pp. 47-64 (2004).*
Chirila, T., et al., Biomaterials, vol. 23, pp. 321-342 (2002).*
Agrawal, S. et al., Molecular Med. Today, vol. 6, pp. 72-81 (2000).*
Crooke, S., Annu. Rev. Med., vol. 55, pp. 61-95 (2004).*
Opalinska, J.B. et al., Nature Rev., vol. 1, pp. 503-514 (2002).*
Branch, A., Trends in Biochem. Sci., vol. 23, pp. 45-50 (1998).*
Torrence, P.F. et al., Proc. Natl. Acad. Sci., vol. 90, pp. 1300-1304 (1993).*

Froehler, B. et al., Triple-Helix Formation by Oligodeoxynucleotides Containing the Carbocyclic Analogs of Thymidine and 5-Methyl-2'-deoxycytidine, *J. Am. Chem. Soc.* vol. 114 (1992) pp. 8320-8322.
Bass, B.L., The Short Answer, *Nature*, vol. 411, May 24, 2001, pp. 428-429.
Jaffe, E. et al., Culture of Human Endothelial Cells Derived From Umbilical Veins, *Journal of Clinical Investigation*, vol. 52, Nvo. (1973) pp. 2745-2756.
Stirchak, E. et al., Uncharged Stereoregular Nucleic Acid Analogs: 2. Morphoiino Nucieoside Oligometers With Carbamate Internucleoside Linkages, *Nucleic Acids Research*, vol. 17, No. 15 (1989) pp. 6129-6141.
Uhlmann, E. et al., Antisense Oligonucleotides: A New Therapeutic Principle, *Chemical Reviews*, vol. 90, No. 4, (Jun. 1990) pp. 543-584.
Uhlmann, E. et al., Oligonucleotide Analogs Containing Dephospho-Internucleoside Linkages, Methods in Molecular Biology, vol. 20, *Protocols for Oligonucleotides and Analogs* (1993) Chapter 16, pp. 355-389.
Uhlmann, E. et al., Synthesis and Properties of PNA/DNA Chimeras, *Angew. Chem. Int. Ed. Engl.*, vol. 35 (1996) pp. 2632-2638.
Vandendriessche, F. et al., Acyclic Oligonucleotides: Possibilities and Limitations, *Tetrahedron*, vol. 49, No. 33 (1993) pp. 7223-7238.
Hunziker, J. et al., Nucleic Acid Analogues: Synthesis and Properties, *Institute for Organic Chemistry*, pp. 331-417.
Engels, J.W. et al., Chemistry of Oligonucleotides, *Pharmaceuticals Aspects of Oligonucleotides* (2000) pp. 35-78.
Koga, M. et al., Alternating alpha, Beta-Oligothymidylaes With Alternating (3'-3')- and (5'-5') Internucleotidic Phosphodiester Linkages As Models for Antisense Oligodeoxyribonucleotides, *Journal of Organic Chemistry*, vol. 56, No. 12 (Jun. 7, 1991) pp. 3757-3759.
Manoharan, M. 2'-Carbohydrate Modifications in Antisense Oligonucleotide Therapy: Importance of Conformation, Configuration and Conjugation, *Biochimica et Biophysica, Acta* vol. 1489 (1999) pp. 117-130.
Player, M.R. et al., The 2-5A System: Modulation of Viral and Cellular Processes Through Acceleration of RNA Degradation, *Pharmacol Ther.* vol. 78, No. 2 (1998) pp. 55-113.
Tarkoy, M. et al., Nucleic-Acid Analogues with Constraint Conformational Flexibility in the Sugar-Phosphate Backbone ('Bycyclo-DNA'), *Helvetica Chimca Acta*, vol. 76 (1993) pp. 481-510.
Weiner, N. et al., Liposomes As A Drug Delivery System, *Drug Development and Industrial Pharmacy*, vol. 15, No. 10 (1989) pp. 1523-1554.
Herdewijn, P., Conformationally Restricted Carbohydrate-Modified Nucleic Acids and Antisense Technology, *Biochimica et Biophysica Acta*, vol. 1489 (1999) pp. 167-179.
Herdewijn, P., Heterocyclic Modifications of Oligonucleotides and Antisense Technology, *Antisense & Nucleic Acid Drug Development*, vol. 10 (2000) pp. 297-310.
Nielsen, P. et al., Peptide Nucleic Acid (PNA). A DNA Mimic With A Peptide Backbone, *Bioconjugate Chem.* (1994) vol. 5, pp. 3-7.
Torrence, P. et al., Targeting RNA for Degradation With a (2'-5')oligodenylate-antisense Chimera, *Proc. Natl. Acad. Sci. USA*, vol. 90 (Feb. 1993) pp. 1300-1304.
Torrence, P.F. et al., Development of 2',5'-Oligonucleotides as Potential Therapeutic Agents, *Current Medicinal Chemistry*, vol. 1 (1994) pp. 176-191.

(Continued)

*Primary Examiner*—Jane Zara

(57) ABSTRACT

The present invention relates to oligoribonucleotide derivatives which have a 2'5'-linked oligoribonucleotide residue without a 5'-phosphate residue on the 3' end and to the use thereof for specific inhibition of gene expression.

21 Claims, No Drawings

OTHER PUBLICATIONS

Iyler, R. et al., Modified Oligonucleotides—Synthesis, Properties and Applications, *Curr. Opin. In Molecular Therapeutics*, vol. 1, No. 3 (1999) pp. 344-358.

Hayashi, S-I. et al., In Vivo Transfer of Gene and Oligodeoxynucleotides Into Skin of Fetal Rats by Incubation in Amniotic Fluid, *Gene Therapy*, vol. 3 (1996) pp. 878-885.

Verma, S. et al., Modified Oligonucleotides: Synthesis and Strategy for Users, *Annu. Rev. Biochem.*, vol. 67 (1998) pp. 99-134.

Singh, S.K. et al., LNA (locked nucleic acids): Synthesis and High-Affinity Nucleic Acid Recognition, *Chem. Commun.* (1998) pp. 1247-1248.

Woolf, T. et al., Specificity of Antisense Oligonucleotides in vivo, *Proc. Natl. Acad. Sci*, USA. vol. 89 (Aug. 1991) pp. 7305-7309.

Leaman et al., Controlling Gene Expression with 2-5A Antisense, Methods: A Comparison to Methods in Enzymology, vol. 18, No. 3, (Jul. 1999) pp. 252-265.

Kandimalla et al., "Mixed backbone antisense oligonucleotides: design, biochemical and biological properties of oligonucleotides containing 2'-5'-ribo- and 3'-5'deoxyribonucleotide segments", *Nucleic Acids Research*, vol. 25, No. 2 (1997) pp. 370-378.

Torrence et al., Oligonucleotide Structural Parameters That Influence Binding of 5'-O-Triphosphoadenylyl-(2'-5')-adenylyl—(2'-5')-adenosine to the 5'-O-Triphosphoadenylyl-(2'-5')-adenylyl—(2'-5')-adenosine Dependent Endoribonuclease: Chain Length????, J. Med. Chem., vol. 27, pp. 726-733 (1984).

Summerton et al., Morpholino Antisense Oligomers, Antisense & Nucleic Acid Drug Development, 7, 187-195, 1997.

* cited by examiner

OLIGORIBONUCLEOTIDE DERIVATIVES FOR SPECIFIC INHIBITION OF GENE EXPRESSION

The present invention relates to novel oligoribonucleotide derivatives which have a 2'5'-linked oligoribonucleotide residue without a 5'-phosphate residue on the 3' end and to the use thereof for specific inhibition of gene expression.

The inhibition of gene expression with the aid of synthetic nucleic acids is becoming increasingly important. Typical representatives of these synthetic nucleic acids (oligonucleotides) are antisense oligonucleotides, ribozymes, DNA enzymes and external guide sequences (EGS). "Antisense oligonucleotides" are short single-stranded nucleic acid derivatives which bind via Watson-Crick base pairing to a complementary messenger ribonucleic acid (mRNA) whose translation into the corresponding protein is to be inhibited. In most cases antisense oligonucleotides exhibit their action according to a mechanism which is supported by cellular ribonuclease H(RNase H); numerous studies have shown evidence for this. RNase H which is present in all cells recognizes a double strand of DNA and RNA and cuts the mRNA complementary to said oligonucleotide via hydrolysis of one or in most cases more phosphodiester bonds. The way in which the oligonucleotides have to be modified in order for activation of RNase H to take place is known and is described, for example, in Uhlmann (2000) Curr. Opin. Drug Discov. Dev. 3, 203-213. Synthetic ribozymes carry this nuclease activity in their sequence. The most common type of ribozyme is the "hammerhead" ribozyme in which the consensus sequence GAAAC which is derived from naturally occurring ribozymes forms the RNase part and the flanking sequences form the antisense oligonucleotide part. DNA enzymes which, however, are not derived from naturally occurring ribozyme motifs but have been found by in-vitro selection, act in a similar way. EGS are synthetic RNA analogs which activate the cellular RNase P and bind via appropriate flanking sequences to the target mRNA and induce a specific mRNA degradation.

A common problem of the inhibition of gene expression with the aid of synthetic oligonucleotides is that it is always necessary to assay a relatively large number of oligonucleotides against various regions of the target nucleic acid, in order to identify an efficient sequence. Furthermore, antisense oligonucleotides often inhibit gene expression only inefficiently or incompletely. Moreover, sequence-unspecific side effects were observed, which may be caused by the fact that even relatively short part sequences of about five bases in length activate RNase H. This is shown, for example, by "Woolf et al. (1992). Proc. Natl. Acad. Sci. U.S.A. 89, 7305-7309)". However, there are also side effects which are caused by interaction of the antisense oligonucleotides with proteins.

Recently, the use of double-stranded RNA for inhibiting gene expression has been described. Double-stranded RNA (dsRNA) is a signal for particular cells and organisms to induce a sequence-specific degradation of mRNA according to a process which is known as RNA interference (RNAi). The RNAi phenomenon was observed in a number of different organisms such as, for example, C. elegans, flies, fungi, plants and mouse embryos. RNAi is believed to be very similar or identical to post-transcriptional gene silencing (PTGS) found in plants. A simple injection of dsRNA of more than 500 base pairs (bp) in length, whose sense-strand sequence is identical to the target mRNA to be inhibited, can specifically inhibit expression of a target gene having the corresponding DNA sequence. This does not impair the expression of nonhomologous genes and the base sequence of the target gene is not altered. RNAi is a post-transcriptional process in which the dsRNA is first cleaved into relatively small fragments which are then probably used for sequence-specific degradation of the target mRNA.

Previously, the gene expression was efficiently inhibited mainly by using dsRNA of more than 100 bp in length. This relatively long dsRNA is accessible only via in-vitro or in-vivo transcription from the corresponding DNA via suitable transcription systems. Another limitation of RNAi with long dsRNA is the fact that only particular organisms such as C. elegans, zebra fish, plants, particular types of fungi, Drosophila, oocytes and embryos of mice allow sequence-specific inhibition by dsRNA, while most animal cells when treated with dsRNA cause apoptosis. Long dsRNA still inhibits gene expression when the sequence homology is from 70 to 90%. For this reason, it is possible in the case of gene families with high sequence homology for misinterpretations of the phenotype to occur by simultaneous inhibition of the expression of a plurality of not completely homologous genes.

The treatment of cells with dsRNA, for example with dsRNA viruses, generally leads to an apoptotic process or to the sequence-unspecific degradation of the mRNA due to induction of a 2'5'-oligoadenylate-synthase activity. The infected cell synthesizes in response to the viral dsRNA trimeric or tetrameric adenylate (2'5'-A) with the unusual 2'5'-phosphodiester-internucleoside bond. 2'5'-A is phosphorylated by cellular kinases on its 5' end and then activates a nuclease called RNase L. 2'5'-A may also be chemically synthesized and be introduced into the cell (Torrence et al. (1994) Curr. Med. Chem 1, 176-191). However, synthetic 2'5'-A activates RNase L only if it has been converted to the 5'-phosphate or 5'-triphosphate form. RNase L activated by 5'-p-2'5'-A (p is phosphate, diphosphate or triphosphate) then degrades the entire RNA of the cell in a sequence-unspecific manner. In addition, it was shown that it is possible to inhibit gene expression sequence-specifically with the aid of antisense oligonucleotide conjugates with a 5'-p-2'5'-A residue. For this purpose, however, it is essential that the 5' end of the 2'5'-A residue is not linked to the oligonucleotide but is present as phosphate, thiophosphate or triphosphate (Torrence et al. (1993) Proc. Natl. Acad. Sci. U.S.A. 90, 1300-4). Furthermore, the target RNA-recognizing oligonucleotide part (antisense part) must be in single-stranded form. For the reasons mentioned above, oligonucleotides having on their 3' ends 2'5'-A residues which consequently have no free 5'-phosphate or triphosphate function have not been described previously as inhibitors of gene expression. The inhibition of gene expression by the single-stranded, 5'-phosphorylated 5'-p-2'5'-A antisense oligonucleotide conjugates is a variation of the antisense principle and is therefore also subject to the limitations of the antisense-oligonucleotide approach. In this connection, the 2'5'-A residue is attached to the 5' end of the oligonucleotide via a spacer (linker) so that the 2' or 3' end of the 2'5'-A residue is present in bound form. The RNA-binding portion preferably comprises DNA (FIGS. 4 to 6 in Torence, Curr. Opin. Mol. Ther. (1999)1, 307).

Recently, oligonucleotides have been used increasingly as tools for studying the function of new genes (functional genomics). The use of antisense oligonucleotides and ribozymes for sequence-specific inhibition of gene expression of new genes coding for proteins with unknown function is made more difficult by the fact that generally a large variety of oligonucleotides of different sequences have to be assayed, and this is a disadvantage in particular for a high-throughput process.

It is therefore an object of the present invention to provide novel chemically modified oligonucleotides with significantly improved inhibition of gene expression, which circumvent the abovementioned limitations of the conventional methods and agents. In particular, gene expression was intended to be inhibited in an RNA interference-like process.

According to the invention, this object is achieved by novel oligonucleotide derivatives which have a 2'5'-linked oligonucleotide residue on the 3' end, which carries no phosphate, thiophosphate or triphosphate group. The sequence of the novel oligonucleotide derivatives is complementary to the RNA sequence whose translation is to be inhibited.

The invention accordingly provides oligonucleotide derivatives of the formula I, $$5'-(N)_x-(Z)_n \qquad \text{Formula I}$$

where

N is naturally or not naturally occurring nucleotides, preferably ribonucleotides, which are at least partly complementary to a target RNA, x is independently 10 to 100, preferably 15 to 45 and particularly preferably 16 to 25, n is 2 to 20, preferably 3 to 10, particularly preferably 3 to 6, Z is naturally or not naturally occurring nucleotides which are linked via a 2'5' internucleoside bond, with the proviso that its homologous target RNA has the following sequence patterns:

$5'-(U)_v-(N')_z-(U)_w$
$5'-(U)_v-(N')_z-UX$
$5'-UX-(N')_z-UX$ and
$5'-(U)_v-(N')_z$ where v and w independently of one another are 2 to 20, preferably 2 to 10, particularly preferably 2 to 6 and z is 15 to 25, preferably 16 to 23 and particularly preferably 19 to 21 and U is uridine, N is adenosine (A), guanosine (G), cytidine (C) or U, and X is A, G or C, preferably A. In a preferred embodiment, N may be a ribonucleotide.

If the gene whose expression is to be inhibited contains, for example, the following DNA sequence 5'-TTTTGMGCGAAGGTTGTGGATCTG (Seq ID No. 1) or the following RNA sequence 5'-UUUUGAAGCGMGGUUGUGGAUCUG (Seq ID No. 2) then the target RNA has the following sequence pattern $5'-(U)_v-(N)_z-UX$, where v is 4, z is 19 and X is G.

Furthermore, preference is given to oligonucleotides of the formula I in which one or more phosphodiester bonds have been replaced, for example by phosphorothioate bonds or N3',P5'-phosphoramidate bonds. Particular preference is given to oligonucleotides of the formula I in which one or more phosphodiester bonds have been replaced by phosphorothioate residues. The phosphorothioate residues are preferably introduced on the 3' ends, the 5' ends and on the internal pyrimidine nucleotides C and U, in particular if several pyrimidine nucleotides succeed one another in the sequence.

A particular embodiment of the invention comprises the use of a mixture of two or more oligonucleotide derivatives in accordance with formula 1 for inhibiting gene expression. The oligonucleotide derivatives in this case may be directed against different regions of an RNA or against the RNA of different genes.

The single-stranded oligonucleotides of the formula I were originally employed as control oligonucleotides for RNAi experiments using short dsRNA. Thus, owing to the single-stranded character, inhibition of gene expression was not expected. Surprisingly, however, particular single-stranded oligonucleotides inhibited gene expression, too, in particular when sufficiently stable toward nucleases. Another surprise was that the oligonucleotides of the formula I in which the 2'5'-linked oligoadenylate residue has no free 5'-phosphate, 5'-thiophosphate or 5'-triphosphate residue inhibited gene expression in a sequence-specific manner. It also came as a complete surprise that in this case the 2'5'-linked oligoadenylate residue can be bound to the 3'5'-linked RNA directly via the 5' function. It has been a valid dogma up until now that the 2'5'-linked oligoadenylate residue must have a free phosphate, thiophosphate or triphosphate residue on the 5' end in order to inhibit gene expression. Moreover, a 2'5' oligoadenylate-mediated inhibition had previously always been associated with an unspecific, i.e. sequence-independent, effect (Bass, Nature (2001) 411, 428). It is therefore obvious that the oligonucleotides of the formula I not only deviate in their structure from the oligonucleotide conjugates described by Torrence (Curr. Opin. Mol. Ther. (1999) 1, 307) but also exhibit a much better inhibitory action which consequently is based on a different mechanism.

Surprisingly, the oligonucleotides of the invention also had an inhibitory sequence-specific effect on human primary cells. As far as we know, the inhibition of gene expression by oligonucleotides having 2'5'-linked nucleotides in human primary cells has not been observed previously.

The inventive oligonucleotides of the formula I may also be used for inhibiting gene expression in cells which express only a small amount of, a defective or no 2'5'-oligoadenylate synthase.

It is furthermore also possible to use the oligonucleotides of the formula I for treating patients having a deficiency or defect in 2'5'-oligoadenylate synthase. Patients with CFS (chronic fatigue syndrome), for example, may also be treated.

The sequences of the oligonucleotides of the formula I which are used for inhibiting the gene expression of particular targets are selected on the basis of the corresponding gene sequences. The sequences of said genes are obtained by sequencing or from gene databases. An example which may be illustrated here is the inhibition of luciferase (firefly) by double-stranded nucleic acids. The accession number for this gene is U47298. The coding region of firefly luciferase comprises 1 653 nucleotides. The following four regions may be selected, inter alia, as target sequences for the inhibition by double-stranded nucleic acids.

```
                                              (Seq ID No. 3)
        gcttttacagatgcacatatcgaggtggacatcacttacg
    121 ---------+---------+---------+---------+    160
        cgaaaatgtctacgtgtatagctccacctgtagtgaatgc (Seq ID No. 4)
        ccgcgaacgacatttataatgaacgtgaattgctcaacag
    311 ---------+---------+---------+---------+    350
        ggcgcttgctgtaaatattacttgcacttaacgagttgtc (Seq ID No. 5)
        gcggtcggtaaagttgttccattttttgaagcgaaggttg
   1081 ---------+---------+---------+---------+   1120
        cgccagccatttcaacaaggtaaaaaacttcgcttccaac (Seq ID No. 6)
        attttttgaagcgaaggqttgtggatctggataccgggaaa
   1101 ---------+---------+---------+---------+   1140
        taaaaaacttcgcttccaacacctagacctatggcccttt
```

The corresponding RNA for these regions then has the following sequence.

```
                                              (Seq ID No. 7)
        GCUUUUACAGAUGCACAUAUCGAGGUGGACAUCACUUACG (Seq ID No. 8)
        CCGCGAACGACAUUUAUAAUGAACGUGAAUUGCUCAACAG
```

```
                                               (Seq ID No. 9)
GCGGUCGGUAAAGUUGUUCCAUUUUUUGAAGCGAAGGUUG (Seq ID No. 10)
AUUUUUUGAAGCGAAGGUUGUGGAUCUGGAUACCGGGAAA
```

The inventive complementary oligonucleotides of the formula I derived therefrom have the following sequences and are characterized in that two or more nucleotides (indicated here by lower-case letters) are linked via a 2'5'-internucleoside bond. Preference is given to 2'5'-linked adenylate residues.

```
3'  aaaaAUGUCUACGUGUAUAGCUCCAC      Seq ID No. 11

3'  aaaaAUAUUACUUGCACUUAACGAG       Seq ID No. 12

3'  aaaaCCAUUUCAACAAGGUAAAAAA       Seq ID No. 13

3'  aaaaaaCUUCGCUUCCAACACCUAGAC     Seq ID No. 14
```

In order to improve metabolic stability, it is also possible to modify the oligonucleotides, for example as phosphorothioates (asterisks). Stabilization by phosphorothioates is preferably carried out on the ends and internal pyrimidine nucleotides.

```
3'                                  (SEQ ID NO:24)
a*a*a a-C*U*U*C G C*U*U C*C A A*C A
C*C*U A G A*C
```

The specificity of the inhibition of luciferase expression can be checked on the basis of control oligonucleotides which are not completely complementary to the target RNA and have, for example, 4 base mismatches.

```
3'                                  Seq ID No. 15
a*a*a a C*U*U*C U*C U*U*C A A C*C
A*C*C G A*G A*C
```

An example of the structure of oligonucleotides of the formula I is given below:

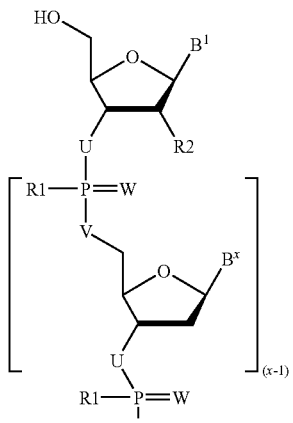

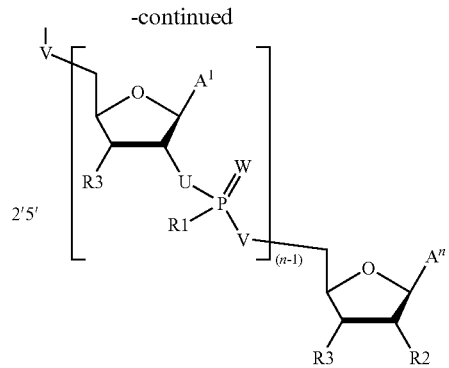

where B is a naturally or not naturally occurring nucleobase,
U, V and W independently of one another are O, S, NH or $CH_2$, preferably O or S,
$R^1$ is independently of one another OH, SH, $CH_3$ or $BH_3$, preferably OH or SH, or physiologically tolerated salts thereof,
$R^2$ is independently of one another OH, H, O—$C_1$ to $C_{12}$-alkyl, preferably OH (ribonucleotide), where $C_1$ to $C_{1-2}$-alkyl preferably is $CH_3$ or $CH_3$—O—$CH_2CH_2$,
$R^3$ is independently of one another OH, H, O—$C_1$ to $C_{12}$-Alkyl, preferably OH or H, where $C_1$ to $C_{1-2}$-alkyl preferably is $CH_3$ or $CH_3$—O—$CH_2CH_2$,
x is independently 10 to 100, preferably 15 to 45, and particularly preferably 16 to 25,
n is 2 to 20, preferably 3 to 10, particularly preferably 3 to 6,
A is adenine or an adenine derivative, for example 8-bromoadenine, 8-methyladenine, or hypoxanthine.

In order to test the inhibition of gene expression using the oligonucleotides of the invention in animal cells, in particular in human primary cells, these are directed, for example, against a human gene or the corresponding RNA thereof and assayed in human cells (HUVEC, human umbilical vein endothelial cells). For this, Edg-1 DNA (accession number M31210) from the gene database, for example, may be transcribed into the corresponding messenger RNA and the following two regions (175 and 725) could be selected for synthesizing appropriate oligonucleotides.

Edg-1 RNA:

```
"175"                                (Seq ID No. 16)
GACCUCGGUGGUGUUCAUUCUCAUGUGCUGCUUUAUCAUCCUGGAGAACA
UCUUUGUCUU

"725"                                (Seq ID No. 17)
AUUUCCAAGGCCAGCCGCAGCUCUGAGAAUGUGGCGCUGCUCAAGACCGU
AAUUAUCGUC
```

Examples of the possible structure of the corresponding oligonucleotides are disclosed below:

```
3'-aaaaUAGUAGGACCUCUUGUAGAAA;       Seq ID No. 18

3'-aaaaGGUUCCGGUCGGCGUCGAGAC;       Seq ID No. 19

Mismatch control
3'-aaaaGGUGCCUGUCUGCGGCGACAC;       Seq ID No. 20
```

The mismatch control differs in 5 nucleotides (underlined as mismatch) from the edg-1 RNA.

Furthermore, the following oligonucleotides directed against edg-1 were prepared, which have improved nuclease stability and increased inhibitory activity and are derived from the above edg-1 sequences.

3'- (SEQ ID NO:18)
a*a*a a U*A G*U A G G A C*C*U C*U*U G*U*A G A A*A

3'- (SEQ ID NO:19)
a*a*a a G G U*U*C*C G G*U*C G G*C G*U*C G A G A*C

3'- (SEQ ID NO:20)
a*a*a a G G U*G C*C*U G*U*C*U G*C G G*C G A*C A*C

The inventive nucleic acid derivatives of formula I are synthesized from oligonucleotides. For example, an oligonucleotide may be synthesized completely from the nucleotides adenosine phosphate, guanosine phosphate, inosine phosphate, cytidine phosphate, uridine phosphate and thymidine phosphate. Preference is given to oligonucleotides which are synthesized from ribonucleotides, the "oligoribonucleotides". In other embodiments of the present invention, an oligonucleotide may contain, where appropriate, one or more modifications, for example chemical modifications. An oligonucleotide may have a plurality of identical and/or different modifications.

The 2'5'-linked residue may contain, for example, adenosine, 3'-deoxyadenosine (cordycepin), inosine, 8-bromoadenosine, 8-methyladenosine and other 8-substituted adenosine derivatives. The ribose residue may also be derivatized as 3'-O-methyladenosine. The internucleoside bonds in the 2'5'-linked portion are preferably phosphodiester and phosphorothioate bonds. Common derivatives of 2'5'-adenylate, their synthesis and activation of RNase L are described in the literature (Player et al. (1998) Pharmacol. Ther. 78, 55).

Examples of chemical modifications are known to the skilled worker and are described, for example, in E. Uhlmann and A. Peyman, Chemical Reviews 90 (1990) 543 and "Protocols for Oligonucleotides and Analogs" Synthesis and Properties & Synthesis and Analytical Techniques, S. Agrawal, Ed, Humana Press, Totowa, USA 1993, J. Hunziker and C. Leumann 'Nucleic Acid Analogs: Synthesis and Properties' in Modern Synthetic Methods (Ed. Beat Ernst and C. Leumann) Verlag Helvetica Chimica Acata, Basle, p. 331-417, R P Iyer et al. *Curr Opin Mol Therap* (1999) 1:344-358; S. Verma and F. Eckstein, *Annu Rev Biochem* (1998) 67:99-134; J W Engels and E. Uhlmann: Chemistry of oligonucleotides. In: *Pharmaceutical aspects of oligonucleotides*. Couvreur P, Malvy C (Eds), Taylor & Francis, London, (2000): 35-78.

The chemical modification of an oligonucleotide may include, for example, a) replacing completely or partially the phosphoric diester bridges with, for example, phosphorothioate, phosphorodithioate, $NR^1R^{1'}$ phosphoramidate, boranophosphate, $(C_1-C_{21})$—O-alkyl phosphate, $[(C_6-C_{12})aryl-(C_1-C_{21})$—O-alkyl] phosphate, $(C_1-C_8)$alkyl phosphonate and/or $(C_6-C_{12})$aryl phosphonate bridges, where
   $R^1$ and $R^{1'}$ independently of one another are hydrogen, $(C_1-C_{18})$alkyl, $(C_6-C_{20})$aryl, $(C_6-C_{14})$aryl-$(C_1-C_8)$alkyl, preferably hydrogen, $(C_1-C_8)$alkyl and/or methoxyethyl, particularly preferably hydrogen, $(C_1-C_4)$alkyl and/or methoxyethyl, or
   $R^1$ and $R^{1'}$, together with the nitrogen atom to which they are bound, form a 5-6-membered heterocycle which may additionally contain another heteroatom selected from the group consisting of O, S, N;

b) replacing completely or partially the 3'- and/or 5'-phosphoric diester bridges with "dephospho" bridges (described, for example, in Uhlmann, E. and Peyman, A. in "Methods in Molecular Biology", Vol. 20, "Protocols for Oligonucleotides and Analogs", S. Agrawal, Ed., Humana Press, Totowa 1993, Chapter 16, 35° ff.), for example with formacetal, 3'-thioformacetal, methylhydroxylamine, oxime, methylenedimethylhydrazo, dimethylenesulfone and/or silyl groups;

c) replacing partially the sugar phosphate backbone, for example with "morpholino" oligomers (described, for example, in E. P. Stirchak et al., Nucleic Acids Res. 17 (1989) 6129 and in J. Summerton and D. Weller, Antisense and Nucleic Acid Drug Dev. 7 (1997) 187-195) and/or with polyamide nucleic acids ("PNAs") (described, for example, in P. E. Nielsen et al, Bioconj. Chem. 5 (1994) 3) and/or phosphomonoester nucleic acids ("PHONAs") (described, for example, in Peyman et al., Angew. Chem. Int. Ed. Engl. 35 (1996) 2632-2638);

d) replacing partially the β-D-ribose units with, for example, β-D-2'-deoxyribose, α-D-2'-deoxyribose, L-2'-deoxyribose, 2'-F-2'-deoxyribose, 2'-F-2'-deoxyarabinofuranose, 2'-O-$(C_1-C_6)$alkylribose, 2'-O-$(C_2-C_6)$alkenylribose, 2'-[O—$(C_1-C_6)$alkyl-O-$(C_1-C_6)$alkyl]ribose, 2'-$NH_2$-2'-deoxyribose, β-D-xylofuranose, β-D-arabinofuranose, α-arabinofuranose, 2,4-dideoxy-β-D-erythrohexopyranose, conformationally restricted sugar analogs such as LNA (Locked nucleic acids; Singh et al., Chem. Commun. 4 (1998) 455; Singh et al. Chem. Commun. 12 (1998) 1247) and carbocyclic (described, for example, in Froehler, J. Am. Chem. Soc. 114 (1992) 8320) and/or open-chain sugar analogs (described, for example, in Vandendriessche et al., Tetrahedron 49 (1993) 7223) and/or bicyclo sugar analogs (described, for example, in M. Tarkov et al., Helv. Chim. Acta 76 (1993) 481). The 2'-modified oligonucleotide analogs are described in detail in Manoharan, Biochim. Biophys. Acta (1999) 117 and conformationally restricted oligonucleotide analogs in Herdewijn, Biochim. Biopyhs. Acta (1999) 167;

e) modifying and, respectively, completely or partially replacing the natural nucleoside bases with, for example, 5-(hydroxymethyl)uracil, 5-aminouracil, pseudouracil, pseudoisocytosine, dihydrouracil, 5-$(C_1-C_6)$alkyluracil, 5-$(C_2-C_6)$-alkenyluracil, 5-$(C_2-C_6)$alkynyluracil, 5-$(C_1-C_6)$alkylcytosine, 5-$(C_2-C_6)$alkenyl-cytosine, 5-$(C_2-C_6)$ alkynylcytosine, 5-fluorouracil, 5-fluorocytosine, 5-chlorouracil, 5-chlorocytosine, 5-bromouracil, 5-bromocytosine or 7-deaza-7-substituted purines.

Heterocyclic base modifications are described, for example, in Herdewijn, Antisense & Nucl. Acid Drug Dev. (2000) 297.

The chemical modification of the oligonucleotide furthermore comprises conjugating an oligonucleotide with one or more molecules which influence advantageously the properties (e.g. nuclease stability, affinity for target sequence, pharmacokinetics) of said oligonucleotide and/or, during hybridization of the modified oligonucleotide to the target sequence, attack said target sequence with binding and/or crosslinking (oligonucleotide conjugates). Examples thereof are conjugates with polylysine, with intercalators such as pyrene, acridine, phenazine, phenanthridine, with fluorescent compounds such as fluorescein, with crosslinkers such as psoralen, azidoproflavin, with lipophilic molecules such as $(C_{12}-C_{20})$alkyl, with lipids such as 1,2-dihexadecyl-rac-glycerol, with steroids such as cholesterol or testosterone, with vitamins such as vitamin E, with poly- or oligoethylene glycol, with $(C_{12}-C_{18})$alkyl phosphate diesters and/or with —O—$CH_2$—CH(OH)—O—$(C_{12}-C_{18})$alkyl. Such molecules may be conjugated at the 5' and/or 3' end and/or within the sequence, for example at a nucleobase. Examples of oligonucleotide conjugates known to the skilled worker are described in Manoharan (2001) Conjugated Oligonucleotides in Antisense technology. In: Crooke (Editor) Antisense Technology. Marcel Dekker, New York.

A specific embodiment of the chemical modification relates to conjugation of the oligonucleotide a) with lipophilic molecules, for example ($C_{12}$-$C_{20}$)alkyl, b) with steroids such as cholesterol and/or testosterone, c) with poly- and/or oligoethylene glycol, d) with vitamin E, e) with intercalators such as pyrene, f) with ($C_{14}$-$C_{18}$)alkyl phosphate diesters and/or g) with —O—$CH_2$—CH(OH)—O—($C_{12}$-$C_{16}$)alkyl.

Another specific embodiment of the chemical modification relates to derivatization of the oligonucleotide, as described in HMR 99/L045, as aryl ester conjugate, for example as FDA conjugate, which derivatization benefits the cellular uptake of said oligonucleotides.

Methods for preparing said oligonucleotide derivatives are known to the skilled worker and described, for example, in Uhlmann, E. & Peyman, A., Chem. Rev. 90 (1990) 543 and/or M. Manoharan in "Antisense Research and Applications", Crooke and Lebleu, Eds., CRC Press, Boca Raton, 1993, chapter 17, p. 303ff. and/or EP-A 0 552 766.

In further specific embodiments of the present invention, the oligonucleotide may have on its 5' end a 5'-5' inversion. This type of chemical modification is known to the skilled worker and described, for example, in M. Koga et al., J. Org. Chem. 56 (1991) 3757. Moreover, the 5' end is a preferred position for conjugating the oligonucleotide with one or more molecules which have a beneficial effect on the properties (for example stability against nucleases, cellular uptake, affinity for the target sequence, pharmacokinetics) of the oligonucleotide.

The invention further provides methods for preparing the oligonucleotides. The oligonucleotides described may be prepared with the aid of various known chemical methods, as described, for example, in Eckstein, F. (1991) "Oligonucleotides and Analogues, A Practical Approach", IRL Press, Oxford. The oligonucleotides may also be prepared by methods which, where appropriate, contain one or more enzymic steps.

The invention furthermore provides the use of the oligonucleotides for modulating and for completely or partially inhibiting the expression of particular target genes, for example for completely or partially inhibiting translation. The invention furthermore relates to the use of said oligonucleotides for modulating and for completely or partially inhibiting expression in cells which have only a small amount of, a defective or no 2'5'-oligoadenylate synthase.

The invention furthermore provides the use of said oligonucleotides as pharmaceuticals or to the use of said oligonucleotides for the production of pharmaceuticals. In particular, it is possible to use said oligonucleotides in pharmaceuticals which are suitable for the prevention and/or treatment of diseases which accompany the expression or overexpression of particular genes.

The invention further provides the use of said oligonucleotides or of pharmaceuticals containing said oligonucleotides for the treatment of diseases in which specific genes are the cause or are involved, due to overexpression.

The pharmaceuticals of the present invention may be used, for example, for the treatment of disorders caused by viruses, for example by CMV, HIV, HSV-1, HSV-2, hepatitis B, hepatitis C viruses, or papillomaviruses. Pharmaceuticals of the present invention are particularly suitable for the treatment of RNA viruses such as, for example, polio viruses, VSV or Influenza virus, in particular also of double-stranded RNA viruses such as reoviruses, for example.

The pharmaceuticals of the present invention are also suitable, for example, for cancer treatment. In this case it is possible, for example, to use oligonucleotide sequences which are directed against targets responsible for the development or growth of cancers. Examples of such targets are:
1) nuclear oncoproteins such as, for example, c-myc, N-myc, c-myb, c-fos, c-fos/jun, PCNA, p120,
2) cytoplasmic/membrane-associated oncoproteins such as, for example, EJ-ras, c-Ha-ras, N-ras, rrg, bcl-2, cdc-2, c-raf-1, c-mos, c-src, c-abl, c-ets,
3) cellular receptors such as, for example, EGF receptor, Her-2, c-erbA, VEGF receptor (KDR-1), retinoid receptors, protein kinase regulatory subunit, c-fms, Tie-2, c-raf-1 kinase, PKC-alpha, protein kinase A (R1 alpha),
4) cytokines, growth factors, extracellular matrix such as, for example, CSF-1, IL-6, IL-1a, IL-1b, IL-2, IL-4, IL-6, IL-8, bFGF, VEGF, myeloblastin, fibronectin,
5) inhibitors of tumor suppressor genes such as, for example, MDM-2.

The pharmaceuticals of the present invention are further suitable, for example, for the treatment of disorders which are influenced by integrins or cell-cell adhesion receptors, for example by VLA-4, VLA-2, ICAM, VCAM or ELAM.

The pharmaceuticals of the present invention are also suitable, for example, for preventing restenosis. In this connection, it is possible to use, for example, oligonucleotide sequences which are directed against targets responsible for proliferation or migration. Examples of such targets are:
1) nuclear transactivator proteins and cyclins such as, for example, c-myc, c-myb, c-fos, c-fos/jun, cyclins and cdc2 kinase,
2) mitogens or growth factors such as, for example, PDGF, bFGF, VEGF, EGF, HB-EGF and TGF-β,
3) cellular receptors such as, for example, bFGF receptor, EGF receptor and PDGF receptor.

The invention further relates to oligonucleotides for the treatment of asthma, with expression of the adenosine-A1 receptor, adenosine-A3 receptor, Bradikinin receptor or of IL-13 being inhibited with the aid of suitable oligonucleotides.

The invention also relates to oligonucleotides, for example, for the treatment of cardiovascular diseases, with, for example, expression of the β1-adrenergic receptor or of a protein from the EDG family such as, for example, Edg-1 being inhibited.

The invention also relates to oligonucleotides, for example, for the treatment of diabetes, with expression of PTP-1B being inhibited, for example.

The pharmaceuticals may be used, for example, in the form of pharmaceutical preparations which may be administered orally, for example in the form of tablets, coated tablets, hard or soft gelatin capsules, solutions, emulsions or suspensions. They may also be administered rectally, for example in the form of suppositories, or parenterally, for example in the form of injection solutions. Pharmaceutical preparations may be produced by processing said compounds in therapeutically inert organic and inorganic carriers. Examples of such carriers for tablets, coated tablets and hard gelatin capsules are lactose, corn starch or derivatives thereof, talc and stearic acid or salts thereof. Carriers suitable for the preparation of solutions are water, polyols, sucrose, invert sugar and glucose. Carriers suitable for injection solutions are water, alcohols, polyols, glycerol and vegetable oils. Carriers suitable for suppositories are vegetable and hardened oils, waxes, fats and semisolid polyols. The pharmaceutical preparations may also contain preservatives, solvents, stabilizers, wetting agents, emulsifiers, sweeteners, colorants, flavorings, salts for modifying the osmotic pressure, buffers, coating agents, antioxidants and, where appropriate, other therapeutically active substances.

Preferred administration forms are topical administrations, local administrations such as, for example, with the aid of a catheter or by inhalation, injections or infusions, and oral administration. For injection, the oligonucleotide derivatives are formulated in a liquid solution, preferably in a physiologically acceptable buffer such as, for example, Hank's solution or Ringer's solution. However, the oligonucleotides may also be formulated in solid form and be dissolved or suspended prior to use. The dosages preferred for systematic administration are from approx. 0.01 mg/kg to approx. 50 mg/kg body weight and day.

The invention furthermore relates to pharmaceutical preparations which contain oligonucleotides and/or physiologically tolerated salts thereof in addition to pharmaceutically suitable carriers and/or additives.

The oligonucleotides and/or physiologically tolerated salts thereof may be administered to animals, preferably to mammals, and in particular to humans as pharmaceuticals on their own, in mixtures with one another or in the form of pharmaceutical preparations which permit topical, percutaneous, parenteral or enteral application and which contain as active ingredient an active dose of at least one oligonucleotide in addition to common pharmaceutically suitable carriers and additives. The preparations normally contain about from 0.1 to 90% by weight of the therapeutically active compound. For the treatment of skin disorders such as, for example, psoriasis or vitiligo, a topical application, for example in the form of ointments, lotions or tinctures, emulsions, or suspensions is preferred.

The pharmaceutical preparations are produced in a manner known per se (e.g. Remingtons Pharmaceutical Sciences, Mack Publ. Co., Easton, Pa.), with pharmaceutically inert inorganic and/or organic carriers being used. For the production of pills, tablets, coated tablets and hard gelatin capsules, lactose, corn starch and/or derivatives thereof, talc, stearic acid and/or salts thereof, etc. may be used, for example. Examples of carriers for soft gelatin capsules and/or suppositories are fats, waxes, semisolid and liquid polyols, natural and/or hardened oils, etc. Examples of carriers suitable for the preparation of solutions and/or syrups are water, sucrose, invert sugar, glucose, polyols, etc. Carriers suitable for the preparation of injection solutions are water, alcohols, glycerol, polyols, vegetable oils, etc. Carriers suitable for microcapsules, implants and/or rods are mixed polymers of glycolic acid and lactic acid. Liposome formulations which are known to the skilled worker (N. Weiner, Drug Develop Ind Pharm 15 (1989) 1523; "Liposome Dermatics, Springer Verlag 1992), for example HVJ liposomes (Hayashi, Gene Therapy. 3 (1996) 878), are also suitable. Dermal administration may also be carried out, for example, with the aid of ionophoretic methods and/or with the aid of electroporation. In addition, it is possible to use lipofectins and other carrier systems, for example those which are used in gene therapy. Particularly suitable systems are those which can be used to introduce oligonucleotides into eukaryotic cells with great efficiency.

In addition to the active substances and the carriers, a pharmaceutical preparation may also contain additives such as, for example, fillers, extenders, disintegrants, binding agents, lubricants, wetting agents, stabilizers, emulsifiers, preservatives, sweeteners, colorants, flavorings or aromatizers, thickening agents, diluents, buffer substances, furthermore solvents and/or solubilizers and/or agents for achieving a depot effect, and also salts for modifying the osmotic pressure, coating agents and/or antioxidants. They may also contain two or more different oligonucleotides and/or their physiologically tolerated salts and furthermore, in addition to at least one oligonucleotide, one or more other therapeutically active substances.

The dose may vary within wide limits and, in each individual case, has to be adjusted to the individual circumstances.

EXAMPLES

1. Synthesis of the Oligonucelotides of the Formula 1
a) 3' aaaaaaCUUCGCUUCCAACACCUAGAC (The bases indicated by lower-case letters have a 2'5'-internucleoside bond). (SEQ ID NO:14)

The syntheses were carried out in an ABI 394 DNA or Expedite synthesizer (Applied Biosystems, Weiterstadt, Germany). The synthesis cycles recommended by the manufacturer were used but for the ribonucleoside-2'-O-phosphoramidites the condensation step was doubled (with a coupling time of in each case 400 s) and the length of the iodine oxidation step was increased to 30 s. The solid phase used was a 1000 Å controlled pore glass (CPG) support which had 5'-O-dimethoxytrityl-N-6-benzoyladenosine (NSS-6101-10A, Chemgenes, Waltham, Mass.) bound via the 2' or 3' position of the sugar. After removing the 5'-O-dimethoxytrityl group by cleavage with trichloroacetic acid, the 2'5'-linked oligonucleotide part was synthesized by five condensations with 5'-O-dimethoxytrityl-N-6-benzoyl-3'-O-tertbutyidimethylsilyladenosine-2'-O-phosphoramidite (ANP-5681, Chemgenes). This was followed by synthesizing the 3'5'-linked oligonucleotide part by repeated condensation with the corresponding 5'-O-dimethoxytrityl-2'-O-tertbutyldimethylsilylnucleoside-3'-O-phosphoramidites (ANP-5671 to ANP-5680, Chemgenes). The CPG support was incubated with 750 μl of conc. ammonia/ethanol (3:1, v:v) with shaking at 30° C. for 24 hours in order to remove the oligomer from the support and to deprotect the phosphate and amino protective groups. The supernatant was separated from the support which was then washed twice more with 150 μl of conc. ammonia/ethanol (3:1, v:v). The combined supernatants were concentrated under reduced pressure and the residue was incubated with shaking in 1200 μl of triethylamine×3HF (very toxic) at 30° C. for 24 hours in order to remove the silyl protective groups. This is followed by adding 700 μl of n-butanol, cooling the mixture on dry ice for 30 minutes and centrifugation. The pellet was washed with butanol two more times. In addition, a sodium chloride precipitation was then carried out. 1120D (260) of the crude product which shows only one main band in gelelectrophoresis were obtained. The product was further characterized by means of HPLC and electrospray mass spectrometry (negative mode) (calc. 8527.2, found 8527.5).

b) 3' (SEQ ID NO:24)
a*a*a a-C*U*U*C G C*U*U C*C A A*C A C*C*U A G A*C

The synthesis was carried out analogously to that of example 1a), with the 2'5'-linked oligonucleotide part being synthesized by three condensations with 5'-O-dimethoxytrityl-N-6-benzoyl-3'-O-tertbutyldimethylsilyladenosine-2'-O-phosphoramidite (ANP-5681, Chemgenes). The phosphorothioate residue was introduced by using the Beaucage reagent (RN-1535, Chemgenes, Waltham, Mass.) rather than the iodine solution in the particular oxidation step. 1280D (260) of the crude product which shows only one main band in gelelectrophoresis were obtained. The product was further characterized by means of HPLC and electrospray mass spectrometry (negative mode) (calc. 8061.6, found 8062.8).

2. Inhibition of Luciferase Expression in SL-3 Cells

In order to test for biological activity, the following oligonucleotides as described in example 1 were prepared and tested for inhibition of luciferase activity.

a)                                                         (SEQ ID NO:14)
3' aaaaaaCUUCGCUUCCAACACCUAGAC b) 3'                                            (SEQ ID NO:24)
a*a*a a-C*U*U*C G C*U*U C*C A A*C A C*C*U A G A*C Transfection: on the day before the experiment, 2×10⁶ cells/ml were plated out into 6-well plates. The oligonucleotides were taken up in 100 µl of SF 900II SFM (SF-900 serum-free insect medium II; Gibco BRL 10902-096). For transfection, 10 µl of lipofectin (1 mg/ml; Gibco BRL) were mixed with 100 µl of SF 900II SFM and incubated at room temperature for 15 min. This was followed by pipetting together the lipofectin mix and the nucleic acid and incubating at room temperature for 15-45 min. In the meantime, the cells were washed with 3 ml of serum-free medium and 800 µl of SF 900II SFM and the nucleic acid/lipofectin mixture were successively added to the cells, followed by incubation at 25 degrees overnight. On the next day, 1 ml of medium and serum (Gibco BRL 10122-166; final concentration 2%) is added.

Dual-luciferase reporter (DLR; Promega E1960) assay system: (http://www.promega.com/catalog/Catalog-Products.asp?catalog %5Fname=Pro mega %5FProducts& category %5Fname=Dual %2DLuciferase+Reporter+Assay+System&description %5Ftext=Dual %2DLuciferase %3Csup %3E %26reg %3B %3 C %2Fsup %3E+Reporter+Assay+System)

The Promega DLR assay allows the sequential determination of the firefly luciferase and *Renilla* luciferase activities having different nucleic acid sequences from a single sample. The oligonucleotides according to the formula I, which were to be measured, were directed against firefly luciferase. Thus, only firefly luciferase activity but not *Renilla* luciferase activity should be inhibited. Thus, apart from the inhibitory action, the specificity may also be tested for.

The passive lysis of the cells in the well plates was carried out by first removing the medium and washing the cells with PBS (phosphate-buffered saline (Gibco BRL 14200-067). The medium was completely removed by suction and then the PLB (passive lysis buffer, diluted 1:5 with water; 500 µl of PLB (1×) to be introduced into one well of a 6-well plate) was added thereto. This was followed by a 15-minute incubation with shaking at room temperature.

The luciferase assay reagent II (LAR II) was prepared by resuspending the luciferase assay substrate (LAS) in 10 ml of luciferase assay buffer II (LAB II). The Stop & Glo reagent was prepared by adding 200 µl of the Stop & Glo substrate (solution) into the bottle containing dry Stop & Glo substrate and mixing the solution for 10 seconds using a vortexer. In order to produce a 1× Stop & Glo solution, 20 µl of the 50× Stop & Glo substrate and 1 ml of the Stop & Glo buffer are combined. This is sufficient for 10 assays.

DLR-assay: 100 µl of LAR II were introduced together with 20 µl of cell lysate into a well and mixed by pipetting up and down for 2-3 seconds. After luminometric measurement of firefly luciferase activity, 100 µl of Stop & Glo reagent were added, the solution was mixed and then the *Renilla*-luciferase activity was determined. The luminescence was determined using the Fluoroskan Ascent FL luminometer (Thermo Labsystems, Frankfurt, Germany).

| Oligonucleotide | % Inhibition* |
|---|---|
| a) 3' aaaaaaCUUCGCUUCCAACACCUAGAC (RNA in antisense orientation, with 2'5' A) | 43 |
| b) 3' a*a*a a-C*U*U*C G C*U*U C*C A A*C A C*C*U A G A*C (RNA in antisense orientation, with 2'5' A) | 43 |
| c) 3' aaaaTTTTTTACCTTGTTGAAATGG (not complementary to target RNA; sense orientation) | 12 |
| d) 3' a*a*a a-C*U*U*C G C*U*U C*CAA* CAC*C*UAGA*C (antisense orientation, underlined 2'-O-methyl) | 7 |
| 5'-G A A G*C G A A G G*U*U G*U G G A U*C*U*G-teg (Seq ID No. 20; sense orientation, without 2'5' A, teg : triethylene glycol phosphate | 0 |
| 3'-teg-G*C*T*T C*C*A A*C A*C*C*T A G A*C*C*T*A (Seq ID No. 21; antisense orientation, DNA, underlined 2'-O-methyl) | 0 |
| 1100 bp dsRNA | 94 |
| without dsRNA | 0 |

% Inhibition of firefly-luciferase activity ( )

The oligonucleotide of a), b) and d) is SEQ ID NO:13 and the oligonucleotide of c) is SEQ ID NO:25.

The firefly luciferase-complementary oligonucleotide a) (SEQ ID NO:14) inhibited firefly-luciferase activity to a substantially greater extent than the non-complementary oligonucleotide c) (SEQ ID NO: 25). The stabilization of the oligonucleotide by phosphorothioate residues (oligonucleotide b) (SEQ ID NO:24) at particular positions on the oligomer resulted in a markedly improved action. When the entire 3'5'-linked complementary sequence was derivatized as 2'-O-methyl derivative, virtually no activity was detectable (oligonucleotide d). (SEQ ID NO: 24)

3. Inhibition of the edg-1 Expression in Human Primary Umbilical Cells (HUVEC).

In order to test the oligonucleotides of the invention for inhibition of gene expression in human primary cells, said oligonucleotides were also directed against a human gene or the corresponding RNA and tested on human cells (HUVEC, human umbilical vein endothelial cells).

The appropriate oligonucleotides were synthesized. The first two sequences are complementary to edg-1 RNA, while the third oligonucleotide has base mismatches.

2:                                                               (SEQ ID NO:26)
5' A U*C A U*C*C*U G G A G A A*C A*U C*U*U*U-teg

3:                                                               (SEQ ID NO:18)
3'-a*a*a a U*A G*U A G G A C*C*U C*U*U G*U*A G A A*A

-continued

```
#5:                                              (SEQ ID NO:27)
5' C*C*A A G G*C*C A G*C*C G*C A G C*U*C*U*G-teg

#6:                                              (SEQ ID NO:19)
3'-a*a*a a G G U*U*C*C G G*U*C G G*C G*U*C G A G
A*C

#7:                                              (SEQ ID NO:28)
5' C*C*A C*G G A C*A G A C*G C*C*G
C*U*G*U*G-teg

#8:                                              (SEQ ID NO:20)
3'-a*a*a a G G U*G C*C*U G*U*C*U G*C
G G*C G A*C
A*C
```

The control oligonucleotides used were the complementary sequences (sense orientation) without 2'5'-oligoadenylate, where * is phosphorothioate; a*a*a a is a 2'5'-linked adenylate (partially modified with *) and teg is triethylene glycol phosphate.

The oligoribonucleotide analogs which had been modified with phosphothioate at particular positions were used in human primary cells as follows, in order to inhibit gene expression of Edg-1 in human cells (HUVEC, human umbilical vein endothelial cells).

Cells (HUVECs) and detection of cellular uptake.

Transfection: 24 h prior to the actual transfection, primary HUVECs (2nd passage, isolated according to Jaffe et al., 1973, J. Clin. Invest 52, pp. 2745), were plated out at a density of 2.5×10$^5$ cells/well in 6-well plates coated with collagen-I from rats (Biocoat, #354400, Becton Dickinson). For transfection, 6 µl of lipofectin (1 mg/ml; Gibco BRL, # 18292-011) were mixed with 200 µl of serum-free Opti-MEM 1 medium (Gibco BRL, 31985-047) and incubated at room temperature for 15 minutes. In a parallel reaction, 10 µM (→final concentration 0.1 µm) or 100 µm (→final concentration 1 µm) of an oligonucleotide solution (in PBS, pH 7.4) was diluted in a ratio of 1:10 with serum-free Opti-MEM 1 medium and mixed with the same volume of preincubated lipofectin solution. After incubation at room temperature for 15 minutes, the volume of said mixture was increased to 2 ml with serum-free Opti-MEM 1 medium and the cell lawn was washed once with PBS and then incubated with said mixture at 37° C., 5% $CO_2$ and 95% humidity for 4 hours. Subsequently, the cell lawn was washed again with PBS and then overlaid with serum-containing EGM medium (CellSystems, # CC-3024+ EGM supplements # CC-3124) and incubated for a further 24 or 48 h. In the case of uptake studies using fluorescently labeled oligonucleotides, the cells were incubated for 4 hours, then fixed with 5% paraformaldehyde (in PBS, pH 7.4) and directly photographed in an inverted fluorescence microscope (Zeiss Axiovert 135M) with its 200-fold magnification using a cooled CCD camera (ORCA-1, Bfi optilas) and excitation through an FITC filter (excitation: 490 nm, emission: 510 nm) and processed via AQM2000 software (Kinetic Imaging).

Western blot analysis: the cells were lysed by washing the cell lawn once with PBS and then overlaying it with 200 µl/well 2× Laemmli buffer (Bio-Rad #161-0737). After incubation at room temperature for five minutes, the cell lysate was collected using a cell scraper (Becton Dickinson, #3085) and, prior to discontinuous 12% SDS polyacrylamide gel electrophoresis (SDS-PAGE, Laemmli et al., 1970, Bio-Rad-Criterion-System #345-0014), heated at 95° C. for 5 minutes and 45 µl of this solution were applied to each slot. The gel was run in 1× Tris/glycine/SDS buffer (Bio-Rad # 161-0732). For the immunoblot, the gel was transferred with the aid of the Bio-Rad criterion Western blot apparatus (#170-4070) to a nitrocellulose (NC) membrane (Amersham # RPN 2020D) in 1× Tris/glycine buffer (Bio-Rad #161-0732, +10% methanol). The NC membrane was then saturated at room temperature for 1 hour using 1×TBS buffer (Bio-Rad # 170-6435), which contained 5% milk powder ("Blotto", Bio-Rad #170-6404) and 0.1% Tween 20 (Bio-Rad # 170-6531). After washing the membrane three times in Blotto-free TBS-Tween (TBST) buffer, the membrane was incubated with the anti-hEDG-1 primary antibody (polyclonal rabbit serum obtained by immunization with the EDG-1-specific peptide sequence obtained by immunization with the EDG-1-specific peptide sequence CKAHRSSVSDYVNYD (SEQ ID NO:23), coupled to KLH and affinity-purified against the above-mentioned peptide sequence) in a 1:50 dilution in TBST-Blotto at 4° C. overnight. After washing three times with TBST, the secondary antibody (anti-rabbit, alkaline phosphatase-coupled, Dianova # 111-055-045) was incubated in a 1:2000 dilution in TBST-Blotto at room temperature for one hour. After another washing step (see above), the ECF ("enhanced chemifluorescence") detection reaction (Amersham #RPN5785) was carried out, and the NC membrane which was covered with clingfilm was incubated with 1 ml of ECF substrate (Amersham Pharmacia #RPN5785) at room temperature for 5 minutes and then detected using a Fluor-Imager 595 scanner (Amersham Pharmacia). The signal was quantified using the ImageQuant software (Amersham Pharmacia) and normalized to the β-tubulin signal which was obtained after destaining (Alpha Diagnostic Kit # 90100) the NC membrane once and incubating the β-tubulin-specific primary antibody (affinity-purified rabbit antibody, Santa Cruz # sc-9104) according to the above-described method.

| Concentration (µM) | EDG-1 protein (% of control) | | | | | |
|---|---|---|---|---|---|---|
| | Oligo #2 (region "175") | Oligo #3 (region "175") | Oligo #5 (region "725") | Oligo #6 (region "725") | Oligo #7 mismatch | Oligo #8 mismatch |
| 0 | 100.0 | 100.0 | 100.0 | 100.0 | 100.0 | 100.0 |
| 0.01 | 87.7 | 51.4 | 98.6 | 47.2 | 89.4 | 128.3 |
| 0.05 | 100.8 | 44.2 | 129.3 | 35.5 | 109.7 | 107.5 |
| 0.1 | 103.0 | 35.5 | 109.4 | 25.1 | 121.8 | 103.6 |
| 0.5 | 119.2 | 40.3 | 107.2 | 27.1 | 95.7 | 85.6 |
| 1.0 | 104.4 | 34.0 | 96.2 | 22.6 | 100.1 | 83.5 |

Treatment of the primary HUVEC cells with the chemically modified single-stranded oligoribonucleotides of the invention led to a dose-dependent inhibition of edg-1 expression. Only the oligoribonucleotides #3 and #6 with antisense orientation inhibited gene expression, while the oligoribonucleotides #2 and #5 with sense orientation did not inhibit expression. The inhibition proved to be target gene-specific, since, after treatment with the edg-1-specific oligoribonucleotides #3 and #6, only the EDG-1 protein levels and not the tubulin level were reduced. The inhibition proved to be also sequence-specific with regard to the oligoribonucleotides used, since only the edg-1-homologous oligoribonucleotides #3 and #6 inhibited edg-1 expression, while the oligoribonucleotide #8 with antisense orientation, which differs from the edg-1 sequence by 5 nucleotides, did not inhibit edg-1 expression.

The invention claimed is:

1. A single strand oligonucleotide of the formula I $$5'-(M)x-(Z)n \qquad \text{Formula I}$$

where

M comprises naturally or not naturally occurring ribonucleotides which are complementary to a target RNA, x is independently 10 to 100, n is 2 to 20, Z comprises naturally or not naturally occurring nucleotides which are linked via a 2'5' internucleoside bond, with the proviso that its homologous target RNA has one of the following sequence patterns:

5'-(U)v-(N)z-(U)w
5'-(U)v-(N)z-UX
5'-UX-(N)z-UX and
5'-(U)v-(N)z, where v is independently 2 to 20,
where w is independently 2 to 20,
z is independently 15 to 25,
U is uridine, N is adenosine (A), guanosine (G), cytidine (C) or U and X is A, G or C, or physiologically tolerated salts thereof.

2. The oligonucleotide of the formula I as claimed in claim 1, wherein x is 15 to 45.

3. The oligonucleotide of the formula I as claimed in claim 2, wherein x is 16 to 25.

4. The oligonucleotide of the formula I as claimed in one of claims 1 to 3, wherein n is 2 to 10.

5. The oligonucleotide of the formula I as claimed in claim 4, wherein n is 3 to 6.

6. The oligonucleotide of the formula I as claimed in one of claims 1 to 3, wherein v is 2 to 10.

7. The oligonucleotide of the formula I as claimed in claim 6, wherein v is 3 to 6.

8. The oligonucleotide of the formula I as claimed in one of claims 1 to 3, wherein w is 2 to 10.

9. The oligonucleotide of the formula as claimed in claim 8, wherein w is 3 to 6.

10. The oligonucleotide of the formula I as claimed in one of claims 1 to 3, wherein z is 16 to 23.

11. The oligonucleotide of the formula I as claimed in claim 10, wherein z is 19 to 21.

12. The oligonucleotide of the formula I as claimed in one of claims 1 to 3, wherein Z is adenosine or 3'-deoxyadenosine.

13. The oligonucleotide of the formula I as claimed in one of claims 1 to 3, in which one or more natural phosphodiester bonds are replaced by unnatural internucleotide bonds which stabilize against nuclease degradation.

14. The oligonucleotide of the formula I as claimed in one of claims 1 to 3, in which one or more natural phosphodiester bonds are replaced by phosphorothioate bonds.

15. The oligonucleotide of the formula I as claimed in one of claims 1 to 3, in which a plurality of natural phosphodiester bonds located on the ends and on internal pyrimidine nucleotides are replaced by phosphorothioate bonds.

16. A method for inhibiting gene expression of a target gene in a cell in vitro comprising one or more oligonucleotides as claimed in one of claims 1 to 3, wherein first an oligonucleotide complementary to an appropriate target gene is prepared, said oligonucleotide is introduced into a cell in vitro, said cell is incubated and inhibition of the gene expression of the target gene is then determined by comparative, measurements of the amount of the corresponding mRNA or corresponding gene product in a control cell.

17. The method as claimed in claim 16 for inhibiting gene expression of a target gene in a cell in which 2'5'-oligoadenylate synthase is underexpressed in comparison with a control cell or is defective.

18. A pharmaceutically compatible composition comprising an oligonucleotide as claimed in one of claims 1 to 3, and additives, carriers, excipients or combinations thereof.

19. A method for preparing an oligonucleotide as claimed in one of claims 1 to 3, wherein the oligonucleotides are first prepared in solution or on the solid phase by successive coupling or coupling in blocks and are, after the preparation, isolated and purified.

20. A method for preparing a pharmaceutically compatible composition, wherein an oligonucleotide derivative as claimed in claim 19 is prepared and admixed with additives, carriers, excipients or combinations thereof.

21. The oligonucleotide of claim 1, 2 or 3, wherein X is A.

* * * * *

UNITED STATES PATENT AND TRADEMARK OFFICE
CERTIFICATE OF CORRECTION

PATENT NO. : 7,635,769 B2 Page 1 of 2
APPLICATION NO. : 11/233907
DATED : December 22, 2009
INVENTOR(S) : Eugen Uhlmann et al.

It is certified that error appears in the above-identified patent and that said Letters Patent is hereby corrected as shown below:

On the title page, item (73), Assignee, in column 1, line 1, delete "Drutschland" and insert -- Deutschland Gmbh --, therefor.

Title page, item (*) Notice: should read as follows: Subject to any disclaimer, the term of this patent is extended or adjusted under 35 U.S.C. 154(b) by 173 days.

On the title page, Other Publications, in column 2, line 7, delete "Clinical-" and insert -- Clinical --, therefor.

On the title page, Other Publications, in column 2, line 25, delete "Pharmaceuticals" and insert -- Pharmaceutical --, therefor.

On the title page, Other Publications, in column 2, line 27, delete "Oligothymidylaes" and insert -- Oligothymidylates --, therefor.

On page 2, Other Publications, in column 1, line 13, delete "1991)" and insert -- 1992) --, therefor.

In column 1, line 20, delete "H(RNase H)" and insert -- H (RNase H) --, therefor.

In column 2, line 56, delete "Torence" and insert -- Torrence --, therefor.

In column 2, line 56, delete "(1999)1 307" and insert -- (1999)307 --, therefor.

In column 3, line 40, delete "5'-TTTTGMGCGAAGGTTGTGGATCTG" and insert -- 5'-TTTTGAAGCGAAGGTTGTGGATCTG --, therefor.

In column 3, line 42, delete "5'-UUUUGAAGCGMGGUUGUGGAUCUG" and insert -- 5'-UUUUGAAGCGAAGGUUGUGGAUCUG --, therefor.

In column 3, line 56, delete "formula 1" and insert -- formula I --, therefor.

Signed and Sealed this

Twenty-seventh Day of July, 2010

David J. Kappos
*Director of the United States Patent and Trademark Office*

In column 5, line 65, delete " 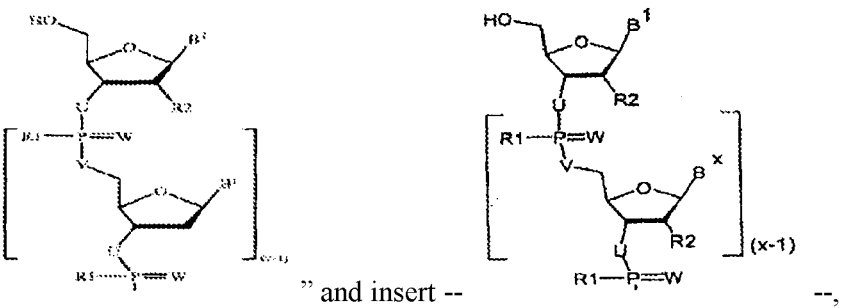 " and insert -- -- , therefor.

In column 6, line 25, delete "$C_{1\text{-}2}$" and insert -- $C_{12}$ --, therefor.

In column 6, line 28, delete "$C_{1\text{-}2}$" and insert -- $C_{12}$ --, therefor.

In column 7, line 57, delete "$C_{1\text{-}8}$" and insert -- $C_{18}$ --, therefor.

In column 8, line 3, delete "35° ff.)" and insert -- 355ff) --, therefor.

In column 11, line 35, delete "Pa.)" and insert -- PA.) --, therefor.

In column 11, line 52, delete "Therapy. 3" and insert -- Therapy 3 --, therefor.

In column 12, line 30-31, delete "tertbutyidimethylsilyladenosine" and insert -- tertbutyldimethylsilyladenosine --, therefor.

In column 12, line 50, delete "1120D" and insert -- 112 OD --, therefor.

In column 12, line 66, delete "1280D" and insert -- 128 OD --, therefor.

In column 13, line 32, delete "Pro mega" and insert -- Promega --, therefor.

In column 15, line 28, delete "24 h" and insert -- 24h --, therefor.

In column 16, line 30-31, before "CKAHRSSVSDYVNYD" delete "obtained by immunization with the EDG-1-specific peptide sequence".

In column 26, line 43, in Claim 9, delete "formula" and insert -- formula I --, therefor.

In column 27, line 3, in Claim 16, delete "comparative," and insert -- comparative --, therefor.

SEQUENCE LISTING

<160> NUMBER OF SEQ ID NOS: 28

<210> SEQ ID NO 1
<211> LENGTH: 25
<212> TYPE: DNA
<213> ORGANISM: Artificial
<220> FEATURE:
<223> OTHER INFORMATION: Part of Photinus pyralis Luciferase

<400> SEQUENCE: 1
ttttgaagcg aaggttgtgg atctg                                     25

<210> SEQ ID NO 2
<211> LENGTH: 25
<212> TYPE: RNA
<213> ORGANISM: Artificial
<220> FEATURE:
<223> OTHER INFORMATION: Part of Photinus pyralis Luciferase

<400> SEQUENCE: 2
uuuugaagcg aagguugugg aucug                                     25

<210> SEQ ID NO 3
<211> LENGTH: 80
<212> TYPE: DNA
<213> ORGANISM: Artificial
<220> FEATURE:
<223> OTHER INFORMATION: Part of Photinus pyralis Luciferase

<400> SEQUENCE: 3
gcttttacag atgcacatat cgaggtggac atcacttacg cgaaaatgtc tacgtgtata    60
gctccacctg tagtgaatgc                                               80

<210> SEQ ID NO 4
<211> LENGTH: 80
<212> TYPE: DNA
<213> ORGANISM: Artificial
<220> FEATURE:
<223> OTHER INFORMATION: Part of Photinus pyralis Luciferase

<400> SEQUENCE: 4
ccgcgaacga catttataat gaacgtgaat tgctcaacag ggcgcttgct gtaaatatta    60
cttgcactta acgagttgtc                                               80

<210> SEQ ID NO 5
<211> LENGTH: 80
<212> TYPE: DNA
<213> ORGANISM: Artificial
<220> FEATURE:
<223> OTHER INFORMATION: Part of Photinus Pyralis Luciferase

<400> SEQUENCE: 5
gcggtcggta aagttgttcc atttttgaa gcgaaggttg cgccagccat tcaacaagg     60

-continued taaaaaactt cgcttccaac                                              80

<210> SEQ ID NO 6
<211> LENGTH: 80
<212> TYPE: DNA
<213> ORGANISM: Artificial
<220> FEATURE:
<223> OTHER INFORMATION: Part of Photinus Pyralis Luciferase

<400> SEQUENCE: 6
attttttgaa gcgaaggttg tggatctgga taccgggaaa taaaaaactt cgcttccaac   60
acctagacct atggcccttt                                              80

<210> SEQ ID NO 7
<211> LENGTH: 40
<212> TYPE: RNA
<213> ORGANISM: Artificial
<220> FEATURE:
<223> OTHER INFORMATION: Part of Photinus Pyralis Luciferase

<400> SEQUENCE: 7
gcuuuuacag augcacauau cgagguggac aucacuuacg                        40

<210> SEQ ID NO 8
<211> LENGTH: 40
<212> TYPE: RNA
<213> ORGANISM: Artificial
<220> FEATURE:
<223> OTHER INFORMATION: Part of Photinus pyralis Luciferase

<400> SEQUENCE: 8
ccgcgaacga cauuuauaau gaacgugaau ugcucaacag                        40

<210> SEQ ID NO 9
<211> LENGTH: 40
<212> TYPE: RNA
<213> ORGANISM: Artificial
<220> FEATURE:
<223> OTHER INFORMATION: Part of Photinus pyralis Luciferase

<400> SEQUENCE: 9
gcggucggua aaguuguucc auuuuuugaa gcgaagguug                        40

<210> SEQ ID NO 10
<211> LENGTH: 40
<212> TYPE: RNA
<213> ORGANISM: Artificial
<220> FEATURE:
<223> OTHER INFORMATION: Part of Photinus pyralis Luciferase

<400> SEQUENCE: 10
auuuuuugaa gcgaagguug uggaucugga uaccgggaaa                        40

<210> SEQ ID NO 11
<211> LENGTH: 26
<212> TYPE: RNA
<213> ORGANISM: Artificial
<220> FEATURE:
<223> OTHER INFORMATION: Part of Photinus pyralis Luciferase

<400> SEQUENCE: 11
caccucgaua ugugcaucug uaaaaa                                       26

<210> SEQ ID NO 12
<211> LENGTH: 25

```
<212> TYPE: RNA
<213> ORGANISM: Artificial
<220> FEATURE:
<223> OTHER INFORMATION: Part of Photinus pyralis Luciferase

<400> SEQUENCE: 12
gagcaauuca cguucauuau aaaaa                                          25

<210> SEQ ID NO 13
<211> LENGTH: 25
<212> TYPE: RNA
<213> ORGANISM: Artificial
<220> FEATURE:
<223> OTHER INFORMATION: Part of Photinus pyralis Luciferase

<400> SEQUENCE: 13
cagauccaca accuucgcuu caaaa                                          25

<210> SEQ ID NO 14
<211> LENGTH: 27
<212> TYPE: RNA
<213> ORGANISM: Artificial
<220> FEATURE:
<223> OTHER INFORMATION: Part of Photinus pyralis Luciferase

<400> SEQUENCE: 14
cagauccaca accuucgcuu caaaaaa                                        27

<210> SEQ ID NO 15
<211> LENGTH: 25
<212> TYPE: RNA
<213> ORGANISM: Artificial
<220> FEATURE:
<223> OTHER INFORMATION: Part of Photinus Pyralis Luciferase

<400> SEQUENCE: 15
cagagccacc aacuucucuu caaaa                                          25

<210> SEQ ID NO 16
<211> LENGTH: 60
<212> TYPE: RNA
<213> ORGANISM: Artificial
<220> FEATURE:
<223> OTHER INFORMATION: Part of human EDG1

<400> SEQUENCE: 16
gaccucggug uguucauuc ucaucugcug cuuuaucauc cuggagaaca ucuuugucuu     60

<210> SEQ ID NO 17
<211> LENGTH: 60
<212> TYPE: RNA
<213> ORGANISM: Artificial
<220> FEATURE:
<223> OTHER INFORMATION: Part of human EDG1

<400> SEQUENCE: 17
auuuccaagg ccagccgcag cucugagaau guggcgcugc ucaagaccgu aauuaucguc    60

<210> SEQ ID NO 18
<211> LENGTH: 25
<212> TYPE: RNA
<213> ORGANISM: Artificial
<220> FEATURE:
<223> OTHER INFORMATION: Part of human EDG1

<400> SEQUENCE: 18
```
aaagauguuc uccaggauga uaaaa                                          25

<210> SEQ ID NO 19
<211> LENGTH: 25
<212> TYPE: RNA
<213> ORGANISM: Artificial
<220> FEATURE:
<223> OTHER INFORMATION: Part of human EDG1

<400> SEQUENCE: 19
cagagcugcg gcuggccuug gaaaa                                          25

<210> SEQ ID NO 20
<211> LENGTH: 25
<212> TYPE: RNA
<213> ORGANISM: Artificial
<220> FEATURE:
<223> OTHER INFORMATION: Part of human EDG1

<400> SEQUENCE: 20
cacagcggcg ucuguccgug gaaaa                                          25

<210> SEQ ID NO 21
<211> LENGTH: 21
<212> TYPE: RNA
<213> ORGANISM: Artificial
<220> FEATURE:
<223> OTHER INFORMATION: Part of Photinus Pyralis Luciferase

<400> SEQUENCE: 21
gaagcgaagg uuguggaucu g                                              21

<210> SEQ ID NO 22
<211> LENGTH: 16
<212> TYPE: RNA
<213> ORGANISM: Artificial
<220> FEATURE:
<223> OTHER INFORMATION: Part of Photinus pyralis Luciferase

<400> SEQUENCE: 22
accagaccac aacccg                                                    16

<210> SEQ ID NO 23
<211> LENGTH: 15
<212> TYPE: PRT
<213> ORGANISM: Artificial
<220> FEATURE:
<223> OTHER INFORMATION: An EDG-1-specific peptide sequence

<400> SEQUENCE: 23

Cys Lys Ala His Arg Ser Ser Val Ser Asp Tyr Val Asn Tyr Asp
1               5                   10                  15

<210> SEQ ID NO 24
<211> LENGTH: 25
<212> TYPE: RNA
<213> ORGANISM: Artificial
<220> FEATURE:
<223> OTHER INFORMATION: Part of Photinus pyralis Luciferase

<400> SEQUENCE: 24
cagauccaca accuucgcuu caaaa                                          25

<210> SEQ ID NO 25
<211> LENGTH: 25
<212> TYPE: DNA

-continued

```
<213> ORGANISM: Artificial
<220> FEATURE:
<223> OTHER INFORMATION: Artificial Nucleotide

<400> SEQUENCE: 25
ggtaaagttg ttccattttt taaaa                                         25

<210> SEQ ID NO 26
<211> LENGTH: 21
<212> TYPE: RNA
<213> ORGANISM: Homo sapiens

<400> SEQUENCE: 26
aucauccugg agaacaucuu u                                             21

<210> SEQ ID NO 27
<211> LENGTH: 21
<212> TYPE: RNA
<213> ORGANISM: Homo sapiens

<400> SEQUENCE: 27
ccaaggccag ccgcagcucu g                                             21

<210> SEQ ID NO 28
<211> LENGTH: 21
<212> TYPE: RNA
<213> ORGANISM: Homo sapiens

<400> SEQUENCE: 28
ccacggacag acgccgcugu g                                             21
```